United States Patent [19]

Goldmann et al.

[11] Patent Number: 5,026,714
[45] Date of Patent: Jun. 25, 1991

[54] NOVEL 1-ALKYL-SUBSTITUTED 1,4-DIHYDROPYRIDINELACTONE ANTI-DIABETICS

[75] Inventors: Siegfried Goldmann; Friedrich Bossert; Hilmar Bischoff, all of Wuppertal; Dieter Petzinna, Wesel; Walter Puls; Klaus Schlossmann, both of Wuppertal, all of Fed. Rep. of Germany

[73] Assignee: Bayer Aktiengesellschaft, Leverkusen, Fed. Rep. of Germany

[21] Appl. No.: 436,157

[22] Filed: Nov. 13, 1989

Related U.S. Application Data

[63] Continuation of Ser. No. 713,053, Mar. 18, 1985, abandoned.

[30] Foreign Application Priority Data

Mar. 23, 1984 [DE] Fed. Rep. of Germany ....... 3410645

[51] Int. Cl.[5] ................ A61K 31/435; C07D 491/048
[52] U.S. Cl. ..................................... 514/302; 546/116
[58] Field of Search ......................... 546/116; 514/302

[56] References Cited

U.S. PATENT DOCUMENTS 4,048,171  9/1977  Bossert et al. ...................... 546/321
4,145,432  3/1979  Sato ..................................... 546/113
4,253,248  7/1985  Franckowiak et al. ............. 546/116

FOREIGN PATENT DOCUMENTS 0111455  6/1984  European Pat. Off. ............. 546/116
3130041  2/1983  Fed. Rep. of Germany .
3206671  9/1983  Fed. Rep. of Germany .

OTHER PUBLICATIONS

Schramm et al., Nature vol. 303, Jun. 9, 1983.

Primary Examiner—Jane T. Fan
Attorney, Agent, or Firm—Sprung Horn Kramer & Woods

[57] ABSTRACT

Novel blood sugar-lowering dihydropyridinelactones of the formula

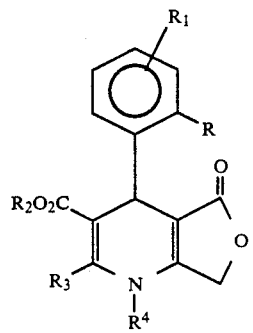

in which
R represents halogen, $C_1$–$C_{10}$-alkyl, $C_1$–$C_{10}$-alkoxy, $C_1$–$C_{10}$-alkylthio, $C_1$–$C_{10}$-alkylsulphinyl, $C_1$–$C_{10}$-alkylsulphonyl, cyano, $C_1$–$C_6$- mono- or polyfluoroalkyl, $C_1$–$C_6$-mono- or polyfluoroalkoxy or nitro,
$R^1$ represents hydrogen, halogen or $C_1$–$C_{10}$-alkyl or $C_1$–$C_{10}$-alkoxy,
$R^2$ represents a $C_1$–$C_{20}$ hydrocarbon radical which can optionally be interrupted or substituted,
$R^3$ represents hydrogen $NH_2$, CHO, CN or a $C_1$–$C_6$ hydrocarbon radical which can be interrupted in the chain, and
$R^4$ represents a $C_1$–$C_{10}$-alkyl or $C_2$–$C_{10}$-alkenyl radical which can optionally be interrupted or substituted with the proviso that R is not $CF_3$ if $R^2$ represents $C_2H_5$.

13 Claims, No Drawings

NOVEL 1-ALKYL-SUBSTITUTED 1,4-DIHYDROPYRIDINELACTONE ANTI-DIABETICS

This is a continuation of application Ser. No. 713,053, filed Mar. 18, 1985, now abandoned.

The present invention relates to new 1,4-dihydropyridinelactones, a process for their preparation, and their use in medicaments.

The new compounds are characterized by the following general formula (I):

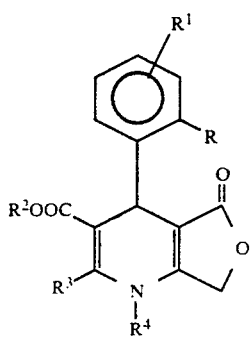

in which
R represents halogen, alkyl (1 to 10 C atoms), alkoxy (1 to 10 C atoms), alkylthio (1 to 10 C atoms), alkylsulphinyl (1 to 10 C atoms), alkylsulphonyl (1 to 10 C atoms), cyano, mono- or polyfluoroalkyl (1 to 6 C atoms), mono- or polyfluoroalkoxy (1 to 6 C atoms) or nitro, $R^1$ represents hydrogen, halogen or alkyl (1 to 10 C atoms) or alkoxy (1 to 10 C atoms), $R^2$ represents a straight-chain, branched or cyclic saturated or unsaturated hydrocarbon radical (1 to 20 C atoms) which can optionally be interrupted by 1 or 2 oxygen atoms or $-SO_n-$ (n=0, 1 or 2) and which can be optionally substituted by one or more fluorine atoms, $-NO_2$, phenyl, $-O-NO_2$, trialkylsilyl (3 to 12 C atoms), $-OH$, $-CN$, amino, monoalkylamino (1 to 6 C atoms), dialkylamino (1 to 6 C atoms each), benzylalkylamino (1 to 6 C atoms), Cl, Br or I, $R^3$ represents hydrogen, $NH_2$, CHO, CN or a straight-chain or branched, saturated or unsaturated hydrocarbon radical (1 to 8 C atoms) which can be interrupted in the chain by oxygen, $-NH-$ or $-N-$alkyl (1 to 6 C atoms), and $R^4$ represents a straight-chain or branched alkyl or alkenyl radical (1 to 10 C atoms) which can optionally be interrupted by one or two oxygen atoms in the alkyl chain and which can optionally be substituted by one or more fluorine atoms, Cl, Br, I, CN, $NH_2$, OH, aryt, hydroxycarbonyl, alkoxycarbonyl (1 to 10 C atoms in the alkoxy radical), $-CHO$, morpholino or dialkylamino (1 to 4 C atoms per alkyl radical), in the form of isomers, isomer mixtures, racemates and optical antipodes, with the restriction that R does not denote $CF_3$ if $R^2$ represents $C_2H_5$.

Of particular interest are compounds of the general formula (I)
in which
R represents halogen, alkyl (1 to 8 C atoms), alkoxy (1 to 8 C atoms), alkylthio (1 to 8 C atoms), alkylsulphinyl (1 to 8 C atoms), cyano, mono- or polyfluoroalkyl (1 to 4 C atoms), mono-or polyfluoroalkoxy (1 to 4 C atoms) or nitro, $R^1$ represents hydrogen, fluorine, chlorine, bromine, alkyl (1 to 6 C atoms) or alkoxy (1 to 6 C atoms), $R^2$ represents a straight-chain, branched or cyclic saturated or unsaturated hydrocarbon radical (1 to 15 C atoms) which can optionally be interrupted by 1 or 2 oxygen or sulphur atoms or $-SO_n-$ (n=1 or 2) and which can optionally be substituted by fluorine, phenyl, $-NO_2$, $-O-NO_2$, trialkylsilyl (3 to 6 C atoms), $-OH$, $-CN$, amino, monoalkylamino (1 to 4 C atoms), dialkylamino (1 to 4 C atoms each), benzylalkylamino (1 to 4 C atoms), Cl or Br, represents hydrogen, CHO, CN, or a straight-chain or branched, saturated or unsaturated hydrocarbon radical (1 to 6 C atoms) which can be interrupted in the chain by $-O-$, $-NH-$ or $-N-$alkyl (1 to 4 C atoms), and $R^4$ represents a straight-chain or branched alkyl or alkenyl radical (1 to 8 C atoms) which can optionally be interrupted by one or two oxygen atoms in the alkyl chain and which can optionally be substituted by one to six fluorine atoms, Cl, Br, CN, $NH_2$, OH, phenyl, naphthyl, hydroxycarbonyl, alkoxycarbonyl, (1 to 6 C atoms in the alkoxy radical), $-CHO$, morpholino or dialkylamino (alkyl radical 1 to 3 C atoms), in the form of isomers, isomer mixtures, racemates and optical antipodes, with the restriction that R does not denote $CF_3$ if $R^2$ represents $C_2H_5$.

Compounds of the general formula (I) which may be preferably mentioned are those
in which
R represents chlorine, fluorine, bromine, alkyl (1 to 6 C atoms), alkoxy (1 to 6 C atoms), alkylthio (1 to 6 C atoms), mono- to hexafluoroalkyl (1 to 3 C atoms), mono- to hexafluoroalkoxy (1 to 3 C atoms) or cyano, $R^1$ represents hydrogen, fluorine, chlorine, alkyl (1 to 4 C atoms) or alkoxy (1 to 4 C atoms), $R^2$ represents a straight-chain, branched or cyclic alkyl or alkenyl radical (1 to 12 C atoms) which can optionally be interrupted by 1 or 2 oxygen or sulphur atoms or $-SO-$ and which can optionally be substituted by fluorine, phenyl, $-NO_2$, $-O-NO_2$, $-OH$, amino, monoalkylamino (1 to 3 C atoms), Cl or Br, $R^3$ represents hydrogen, CN, or a straight-chain or branched alkyl or alkenyl radical (1 to 4 C atoms) which can be interrupted in the chain by O or -N(alkyl)-(1 to 3 C atoms), and $R^4$ represents a straight-chain or branched alkyl or alkenyl radical (1 to 6 C atoms) which can optionally be interrupted by one or two oxygen atoms in the alkyl chain and which can optionally be substituted by 1 to 3 fluorine atoms, Cl, $NH_2$, OH, phenyl, hydroxycarbonyl, alkoxycarbonyl (1 to 3 C atoms in the alkoxy radical), $-CHO$ or morpholino, in the form of isomers, isomer mixtures, racemates and optical antipodes, with the restriction that R does not denote $CF_3$ if $R^2$ represents $C_2H_5$.

Compounds which may be mentioned in particular are those of the general formula (I)
in which
R represents trifluoromethyl, cyano, chlorine, fluorine, bromine, $C_1-C_3$ alkyl or $C_1-C_3$-alkylthio, $R^1$ represents hydrogen or chlorine, $R^2$ represents $C_1$-$C_6$ alkyl which is optionally interrupted by O, S or —SO—, or represents phenyl-$C_1$-$C_2$-alkyl, $R^3$ represents an alkyl radical (1 to 3 C atoms) which can be interrupted in the chain by —O— or

and $R^4$ represents $C_1$-$C_3$ alkyl, $C_2$-$C_3$ alkylene, or $C_1$-$C_3$ alkoxycarbonyl or hydroxycarbonyl, with the exception that R does not denote $CF_3$ if $R^2$ represents ethyl.

The compounds according to the invention, of the general formula (I) can be prepared by (A) deprotonating 1,4-dihydropyridinelactones of the general formula II

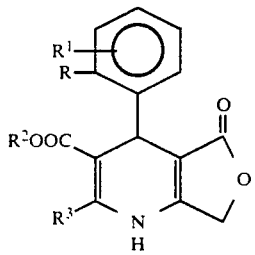

(II)

in which R, $R^1$, $R^2$ and $R^3$ have the abovementioned meaning, with bases in inert solvents and alkylating the resulting deprotonation products with compounds of the general formula I $R^4$—X    (III), in which $R^4$ has the abovementioned meaning and X represents a group which can readily be split off, such as Cl, Br, I or —$OSO_2$—$R^5$, wherein $R^5$ denotes alkyl or aryl, or by (B) reacting aldehydes of the general formula IV

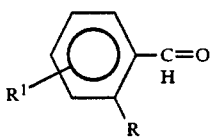

(IV)

in which R and $R^1$ have the abovementioned meaning, and amines of the general formula V, $H_2N$—$R^4$    (V)

in which $R^4$ has the abovementioned meaning, or salts thereof, with keto compounds of the general formula VI

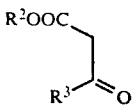

(VI)

in which $R^2$ and $R^3$ have the abovementioned meaning, and tetronic acid of the formula VII

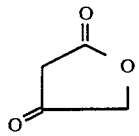

(VII)

if appropriate in the presence of water and/or inert organic solvents, or by (C) reacting aldehydes of the formula IV with keto compounds of the formula VI and enamines of the general formula VIII

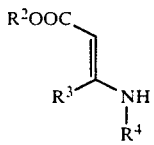

(VIII)

in which $R^4$ has the abovementioned meaning, if appropriate in the presence of water and/or inert organic solvents, or by (D) reacting enamines of the general formula IX

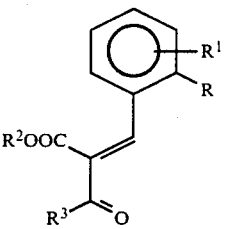

(IX)

in which $R^2$, $R^3$ and $R^4$ have the abovementioned meaning, with aldehydes of the formula IV and tetronic acid of the formula VII, if appropriate in the presence of water and/or inert organic solvents, or by (E) reacting ylidene compounds of the general formula X (X)

in which $R^1$, $R^2$ and $R^3$ have the abovementioned meaning, with enamines of the formula VIII, if appropriate in the presence of water and/or inert organic solvents, or by (F) reacting enamines of the formula IX with ylidene compounds of the general formula XI

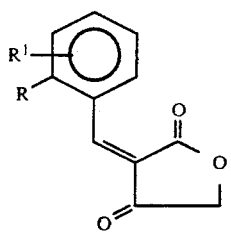
(XI)

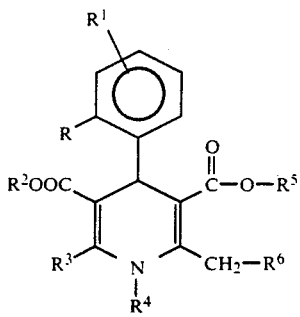
(XII)

in which R and $R^1$ have the abovementioned meaning, if appropriate in the presence of water or inert organic solvents, or by (G) reacting amines of the formula V with ylidene compounds of the formula X and tetronic acid of the formula VII, if appropriate in the presence of water and/or inert organic solvents, or by (H) reacting amines of the formula V with keto compounds of the formula VI and ylidene compounds of the formula XI, if appropriate in the presence of water and/or inert organic solvents, or by (I) cyclizing dihydropyridines of the general formula XII in which R, $R^1$, $R^2$, $R^3$ and $R^4$ have the abovementioned meaning, $R^5$ represents the same meaning as $R^2$ and $R^6$ represents halogen, preferably chlorine or bromine, or the group —O—$R^7$, wherein $R^7$ denotes a customary alcohol protective group, if appropriate in the presence of an inert organic solvent and a suitable auxiliary.

Depending on the type of starting compounds used the variants can be carried out according to the following equations:

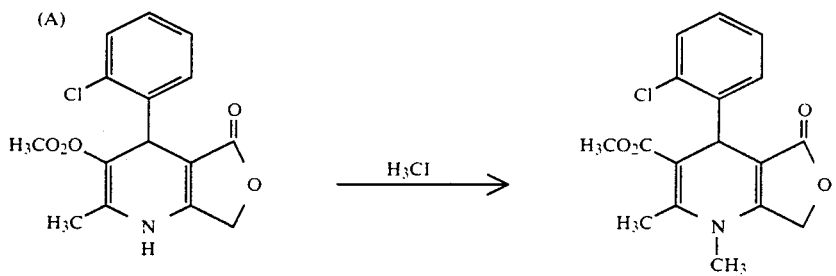

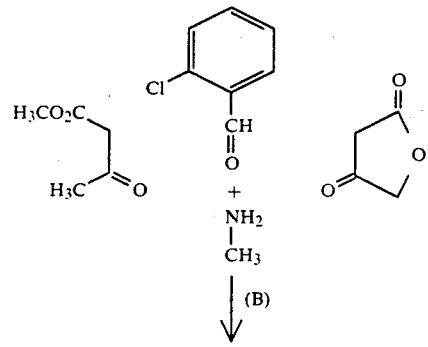

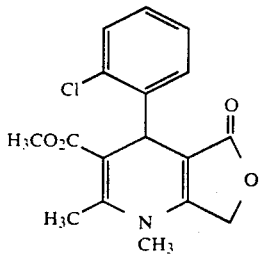

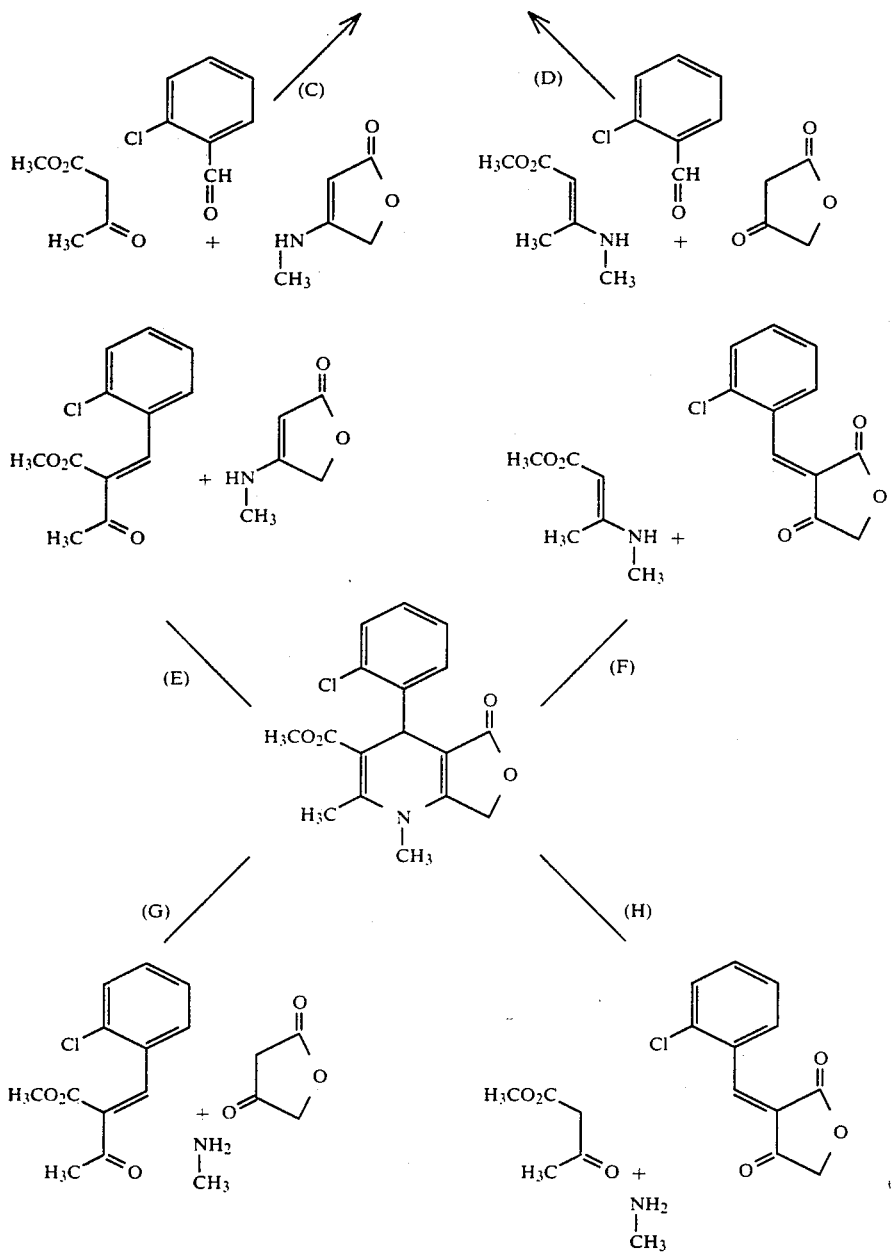

Any of the customary inert solvents can be used as solvents for variant A. Preferred solvents are acid amides such as dimethylformamide, hexamethylphosphoric triamide, ethers such as tetrahydrofuran and dioxane, and sulphoxides such as dimethyl sulphoxide or sulpholane. The bases which can be used in variant A are, for example, metal hydrides such as sodium hydride and potassium hydride, or amides such as sodium amide, 4-diisopropylamide and potassium diethylamide or metal alkyls such as butyl lithium and phenyl lithium, or hydroxides such as potassium hydroxide and sodium hydroxide or alcoholates such as potassium tert.-butanolate and potassium methylate or carbonates such as potassium carbonate.

The alkylation is carried out at temperatures of $-20°$ C. to 180° C., preferably from room temperature to the boiling point of the solvent used.

The alkylation is usually carried out under normal pressure, but pressure can, if appropriate, be applied.

The reactants can be employed in any desired ratio, preferably in a molar ratio.

The possible solvents for variants B–H are water and any inert organic solvents. These are preferably alcohols such as methanol, ethanol, isopropanol, or ethers such as diethyl ether, dioxane or tetrahydrofuran, or glacial acetic acid, pyridine, dimethylformamide, dimethyl sulphoxide, hexamethylphosphoric triamide or acetonitrile.

The variants B–I are carried out at temperatures of 0° C. to 200° C., preferably 20° C. to 150° C.

Normal pressure is usually employed, but elevated pressure can also, if appropriate, be applied.

When carrying out the variants B–H according to the invention the reactants can be employed in any desired ratio. However, the reactants are usually employed in molar ratios.

The cyclization (variant I) can be carried out with our without solvents. If solvents are used these can be any of the customary inert organic solvents. These are preferably aromatic hydrocarbons such as benzene, toluene or xylene, tetralin, petroleum fractions, ethers such as dioxane tetrahydrofuran, glycol mono- or diethyl ether, halogenated hydrocarbons such as di-, tri- or tetrachloromethane, di- or trichloroethylene, or diglyme.

The cyclization can be carried out under normal, elevated or reduced pressure. In general normal pressure is used.

Acids, bases, fluoride or hydrogen can, if required, be used as auxiliaries in variant (I).

The synthesis of the 1,4-dihydropyridinelactones II used as starting compounds is described in European Patent No. 71,819.

The compounds of formulae III to XI used as starting compounds are known from the literature or can be prepared by methods known from the literature (cf. A. C. Cope, J. Am. Chem. Soc. 67, 1017 (1945); U.S. Pat. No. 3,758,515; Organic Reactions XV, 204 et seq (1907); D. Borrmann, "Umsetzungen von Diketen mit Alkoholen, Phenolen und Mercaptanen" (Reactions of diketen with alcohols, phenols and mercaptans), in Houben-Weyl, Methoden der organischen Chemie, Vol. VII/4, 230 et seq. (1968); J. Org. Chem. 43, 1541 (1978); Z. Chem. 10, 341 (1970); Surrey et al. J. Am. Chem. Soc. 66, 1933 (1944); German Offenlegungsschrift 3 207 982.

The starting compounds of the general formula XII (variant I), in which $R^6$ represents the group $-O-R^7$, are known or can be prepared by known methods. Starting compounds of the formula XII in which $R^6=$ halogen, preferably chlorine or bromine, are new and can be prepared by reacting 1,4-dihydropyridines of the general formula XIII

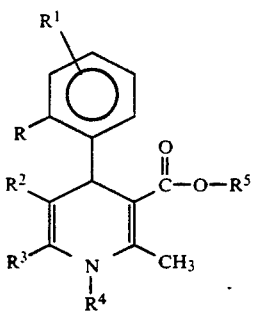

(XIII)

in which R, $R^1$, $R^2$, $R^3$, $R^4$ and $R^5$ have the abovementioned meaning, with halogenating agents in the presence of inert organic solvents, if appropriate in the presence of radical-forming agents.

The possible solvents are any inert organic solvents, but preferably halogenated hydrocarbons such as di-, tri- or tetrachloromethane.

The customary halogenating agents can be used as halogenating agents. Chlorine, bromine, N-chlorosuccinimide or N-bromosuccinimide, are preferred, if appropriate in the presence of radical-forming agents such as a zobisisobutyronitrile, dibenzoyl peroxide or light.

The reaction temperatures can be varied within a wide range. In general the reaction is carried out at between 0° C. and 120° C., preferably at the boiling point of the solvent used.

The reaction can be carried out under normal pressure, but also under elevated pressure. In general normal pressure is used.

The reactants can be used in any desired quantity ratio to one another, but equimolar quantities are preferably used.

The compounds according to the invention of the general formula (I) have a valuable pharmacological action spectrum.

While having only a slight action on circulation, they lower the blood sugar level and can therefore be employed for the treatment of diabetes.

The compounds according to the invention can be converted in a known manner into the customary formulations, such as tablets, capsules, dragees, pills, granules, aerosols, syrups, emulsions, suspensions and solutions, using inert, non-toxic, pharmaceutically suitable excipients or solvents. The therapeutically active compound should in each case be present in a concentration of about 0.5 to 90% by weight of the total mixture, that is to say in amounts which suffice to achieve the indicated dosage range.

The formulations are prepared, for example, by extending the active compounds with solvents and/or excipients, using emulsifiers and/or dispersing agents if appropriate, and, for example in the case of water being employed as the diluent, organic solvents can be used as auxiliary solvents if appropriate.

As examples of auxiliary substances there may be mentioned: water, non-toxic organic solvents, such as paraffins (for example petroleum fractions), vegetable oils (for example groundnut oil/sesame oil), alcohols (for example ethyl alcohol and glycerol), glycols (for example propylene glycol and polyethylene glycol), solid excipients such as, for example, natural rock powders (for example kaolins, aluminas, talc and chalk), synthetic rock powders (for example highly disperse silica and silicates), and sugars (for example cane sugar, lactose and glucose), emulsifiers (for example polyoxyethylene-fatty acid esters, polyoxyethylene-fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, especially perlingually or intravenously. In the case of oral use, tablets can of course also contain, in addition to the excipients mentioned, additives such as sodium citrate, calcium carbonate and dicalcium phosphate, together with various further substances such as starch, preferably potato starch, gelatine and the like. Furthermore, lubricants such as magnesium stearate, sodium lauryl-sulphate and talc can be used conjointly for tablet-making. In the case of aqueous suspensions and/or elixirs which are intended for oral use the active compounds can be mixed with various flavor-improving agents or dyestuffs in addition to the abovementioned auxiliaries.

In the case of parenteral application, solutions of the active compounds can be employed, using suitable liquid excipients.

In general it has proved advantageous, in the case of oral administration, to administer amounts of about 0.01 to 200 mg/kg, preferably 0.1 to 50 mg/kg of body weight to achieve effective results.

Nevertheless it can at times be necessary to deviate from the amounts mentioned and in particular to do so as a function of the body weight of the test animal or of the nature of the administration route, but also because of the type of animal and its individual behavior towards the medicine or the kind of animal's nature of the formulation and the time or interval at which it is administered. Thus it may suffice, in some cases, to manage with less than the abovementioned minimum amount whilst in other cases the upper limit mentioned must be exceeded. Where major amounts are administered it can be advisable to divide these into several administrations over the course of the day. The same dosage range is envisaged for administration in human medicine. Here, again, the general sense of the above comments applies.

EXAMPLE 1

Methyl 1-ethyl-2-methyl-4-(2-trifluoromethylphenyl)-5-oxo-1,4,5,7-tetrahydrofuro-[3,4-b]pyridine-3-carboxylate 50 mmol of methyl 2-methyl-4-(2-trifluoromethylphenyl)-5-oxo-1,4,5,7-tetrahydrofuro-[3,4-b]pyridine-3-carboxylate are dissolved in 100 ml of anhydrous tetrahydrofuran, and 50 mmol of sodium hydride are added. After 10 minutes at room temperature, 55 mmol of ethyl iodide are added, and the mixture is boiled under reflux for 1 hour. The mixture is evaporated down, after which the residue is taken up with $CH_2Cl_2$, the solution is washed with water, dried and evaporated down, and the residue is recrystallized.

M.p.: 150°–152° C.

EXAMPLE 2

Methyl 1-allyl-2-methyl-4-(2-trifluoromethylphenyl)-5-oxo-1,4,5,7-tetrahydrofuro-[3,4-b]pyridine-3-carboxylate Preparation analogous to Example 1, except that dimethylformamide is used as the solvent, and allyl bromide as the alkylating agent.

M.p.: amorphous substance.

$^1$H-NMR (CDCl$_3$): δ=2.4 (s, 3H), 3.5 (s, 3H), 4.1 (m, 2H), 4.7 (s, 2H), 5.4 (d, 2H), 5.8–6.0 (m, 1H) 7.3–7.7 (m, 4H) ppm.

EXAMPLE 3

Ethyl 4-(2-chlorophenyl)-1-ethyl-2-methyl-5-oxo-1,4,5,7-tetrahydrofuro-[3,4-b]pyridine-3-carboxylate 50 mmol of ethyl 4-(2-chlorophenyl)-2-methyl-5-oxo-1,4,5,7-tetrahydrofuro-[3,4-b]pyridine-3-carboxylate are dissolved in tetrahydrofuran, and 50 mmol of lithium diisopropylamide followed by 50 mmol of ethyl iodide are added at −78° C. The mixture is heated to room temperature and stirred for 1 hour, and is worked up analogously to Example 1.

M.p.: 140°–141° C.

EXAMPLE 4

Propyl 4-(2-chlorophenyl)-1,2-dimethyl-5-oxo-1,4,5,7-tetrahydrofuro-[3,4-b]pyridine-3-carboxylate 50 mmol of propyl 4-(2-chlorophenyl)-2-methyl-5-oxo-1,4,5,7-tetrahydrofuro-[3,4-b]pyridine-3-carboxylate are dissolved in 150 ml of dimethyl sulphoxide, and 7 g of potassium hydroxide powder and 50 mmol of methyl iodide are added. After 2 hours at room temperature, the mixture is poured onto ice-water and extracted with $CH_2Cl_2$, the extract is dried and evaporated down, and the residue is recrystallized.

M.p.: 173°–177° C.

---

The following are prepared analogously:

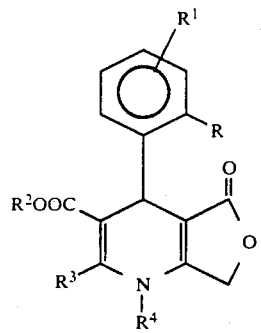

| Example | R | $R^1$ | $R^2$ | $R^3$ | $R^4$ | m.p. | Analogous to Example |
|---|---|---|---|---|---|---|---|
| 5 | —Cl | H | —C$_2$H$_5$ | —CH$_3$ | —CH$_2$—CH=CH$_2$ | 132° | 1 |
| 6 | —Cl | H | —CH$_3$ | —CH$_3$ | —CH$_2$—CH$_3$ | 137-9° | 1 |
| 7 | —Cl | H | —(CH$_2$)$_3$—CH$_3$ | —CH$_3$ | —CH$_2$—CH$_3$ | 169-74° | 1 |
| 8 | —Cl | H | —CH$_2$—CH$_3$ | —CH$_3$ | —(CH$_2$)$_2$—CH$_3$ | 136-9° | 2 |
| 9 | —Cl | H | —CH(CH$_3$)$_2$ | —CH$_3$ | —CH$_2$—CH$_3$ | 110-12° | 3 |
| 10 | —Cl | H | —(CH$_2$)$_2$—OCH$_3$ | —CH$_3$ | —CH$_2$—CH$_3$ | 145° | 1 |
| 11 | —Cl | H | —(CH$_2$)$_2$—S—CH$_3$ | —CH$_3$ | —CH$_2$—CH$_3$ | 131-35° | 1 |
| 12 | CH$_3$ | H | —C$_2$H$_5$ | —CH$_3$ | —C$_2$H$_5$ | 103-10° | 1 |
| 13 | —Cl | H | —(CH$_2$)$_2$—CH$_3$ | —CH$_3$ | —C$_2$H$_5$ | 146-50° | 1 |
| 14 | —Cl | 3-Cl | —C$_2$H$_5$ | —CH$_3$ | —C$_2$H$_5$ | 123-5° | 2 |

-continued

The following are prepared analogously:

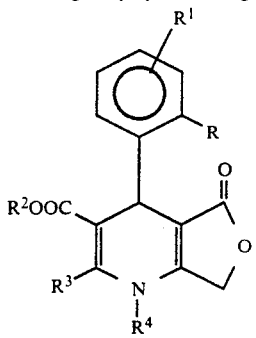

| Example | R | $R^1$ | $R^2$ | $R^3$ | $R^4$ | m.p. | Analogous to Example |
|---|---|---|---|---|---|---|---|
| 15 | —Cl | H | —(CH$_2$)$_2$—C$_6$H$_5$ | —CH$_3$ | —C$_2$H$_5$ | 87° | 2 |
| 16 | —Cl | 6-Cl | —C$_2$H$_5$ | —CH$_3$ | —C$_2$H$_5$ | 130° | 3 |
| 17 | —Cl | 4-Cl | —C$_2$H$_5$ | —CH$_3$ | —C$_2$H$_5$ | 121-4° | 3 |
| 18 | —Cl | H | —(CH$_2$)$_2$—S(O)—CH$_3$ | —CH$_3$ | —C$_2$H$_5$ | amorphous[1] | 1 |
| 19 | —Cl | H | —(CH$_2$)$_5$—CH$_3$ | —CH$_3$ | —C$_2$H$_5$ |  | 1 |
| 20 | —F | H | —C$_2$H$_5$ | —CH$_3$ | —C$_2$H$_5$ | 183-6° | 1 |
| 21 | —SCH$_3$ | H | —C$_2$H$_5$ | —CH$_3$ | —C$_2$H$_5$ | 123-6° | 1 |
| 22 | —Br | H | —C$_2$H$_5$ | —CH$_3$ | —C$_2$H$_5$ | 141-3° | 1 |
| 23 | —Cl | H | —C$_2$H$_5$ | —CH$_3$ | —CH$_2$—COOH | 135-139° | 1 |
| 24 | —Cl | H | —C$_2$H$_5$ | —CH$_3$ | —CH$_2$—COOC$_2$H$_5$ | amorphous | 1 |
| 25 | —Cl | H | —C$_2$H$_5$ | —CH$_2$—OCH$_3$ | —CH$_3$ | 134-7° | 1 |
| 26 | —Cl | H | —C$_2$H$_5$ | —CH$_2$—CH$_2$—N(CH$_3$)$_2$ | —C$_2$H$_5$ | 144-7° | 1 |
| 27 | —Cl | H | —(CH$_2$)$_2$—OC$_2$H$_5$ | —CH$_3$ | —CH$_3$ | 147-9° | 1 |
| 28 | —Cl | H | —(CH$_2$)$_2$—OC$_2$H$_5$ | —CH$_3$ | —CH$_2$—CH$_3$ | 120-2° | 1 |
| 29 | —CH$_3$ | H | —(CH$_2$)$_2$—OCH$_3$ | —CH$_3$ | —CH$_2$—CH$_3$ | 151-4° | 1 |
| 30 | —Cl | H | —(CH$_2$)$_2$—OCH$_3$ | —CH$_3$ | —CH$_3$ | 171-3° | 1 |
| 31 | —Cl | H | —(CH$_2$)$_2$—OCH$_3$ | —CH$_3$ | —CH$_2$—CH=CH$_2$ | 99-100° | 1 |
| 32 | —Cl | H | —(CH$_2$)$_2$—O—(CH$_2$)$_2$—OCH$_3$ | —CH$_3$ | —CH$_3$ | 115-7° | 1 |
| 33 | —Cl | H | —C(CH$_3$)$_3$ | —CH$_3$ | —CH$_2$—CH$_3$ | 131-3° | 1 |
| 34 | —Cl | H | —(CH$_2$)$_2$—CH$_3$ | —CH$_3$ | —CH$_2$—CH$_3$ | 133-5° | 1 |
| 35 | —CH$_3$ | H | —CH(CH$_3$)$_2$ | —CH$_3$ | —CH$_2$—CH$_3$ | 100-3° | 1 |
| 36 | —CN | H | —CH(CH$_3$)$_2$ | —CH$_3$ | —CH$_2$—CH$_3$ | 152-5° | 1 |

[1]MS: 423 (M$^+$), 406 (90%), 378, 332, 316, 312, 288, 248, 222, 177, 75

The action of the substances to be investigated, in respect of their lowering of the blood glucose level, was tested on male Wistar rats weighing between 140 and 190 g. For this purpose, the rats were weighed 18 hours before administration of the substances, and were divided into groups of 6 animals and made to fast. The substances to be investigated were suspended, directly before administration, in an aqueous 0.75% strength tragacanth suspension by means of an Ultra-Turrax. The tragacanth suspension (control animals) or the substances suspended in tragacanth were administered by means of a gavage.

For each rat, blood was withdrawn from the post-orbital venous plexus 30, 60 and 120 minutes after administration. 30 μl samples of blood were taken by means of an automatic dilutor, and were deproteinised with 0.3 ml of uranyl acetate (0.16%). After centrifuging, the glucose in the supernatant liquid was determined photometrically in a Gemsaec Fastanalyser by the glucose oxidase method, using 4-amino-phenazone as a color reagent. Evaluation of the results was carried out by means of Student's t test, the significance limit chosen being $p < 0.05$.

Substances which, at some point in time, effected a significant reduction in the blood glucose concentration in rats by at least 10%, compared with the control group which received only tragacanth suspension, were stated to be effective.

Table 1 below contains the changes found in the blood glucose concentrations as a percentage of the control.

TABLE 1

| Substance (Patent Example No.) | Decrease in the blood glucose concentration as a percentage of the control 30 mg/kg p.o. |
|---|---|
| 3 | 23 |
| 5 | 19 |
| 10 | 26 |
| 12 | 19 |
| 17 | 28 |

It is understood that the specification and examples are illustrative but not limitative of the present invention and that other embodiments within the spirit and scope of the invention will suggest themselves to those skilled in the art.

We claim:

1. A dihydropyridinelactone of the formula

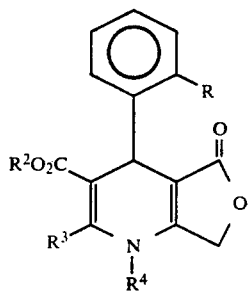

in which

R represents chlorine, bromine, cyano or $C_1$–$C_3$-alkyl, $R^2$ represents straight or branched $C_1$–$C_6$-alkyl which is optionally interrupted by oxygen, $R^3$ represents $C_1$–$C_3$-alkyl, and $R_4$ represents $C_1$–$C_3$-alkyl.

2. A dihydropyridinelactone according to claim 1, in which

R represents chlorine, bromine or methyl, $R^2$ represents $C_1$–$C_6$-alkyl which is optionally interrupted by oxygen, $R^3$ represents methyl, and $R^4$ represents $C_1$–$C_3$-alkyl.

3. A dihydropyridinelactone according to claim 2, in which $R^4$ represents ethyl.

4. A compound according to claim 1, wherein such compound is ethyl 4-(2-chlorophenyl)-1-ethyl-2-methyl-5-oxo-1,4,5,7-tetrahydrofuro[3,4-b]pyridine-3-carboxylate of the formula

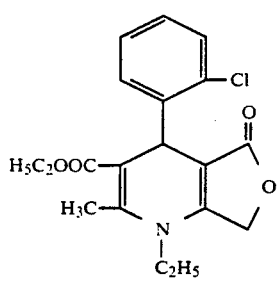

5. A compound according to claim 1, wherein such compound is isopropyl 4-(2-chlorophenyl)-1-ethyl-2-methyl-5-oxo-1,4,5,7-tetrahydrofuro[3,4-b]pyridine-3-carboxylate of the formula

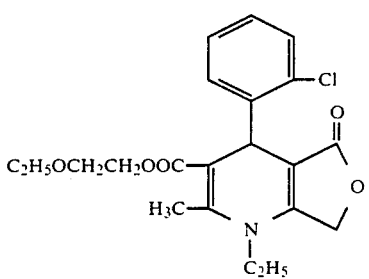

6. A compound according to claim 1, wherein such compound is ethoxyethyl 4-(2-chlorphenyl)-1-ethyl-2-methyl-5-oxo-1,4,5,7-tetrahydrofuro[3,4-b]pyridine-3-carboxylate of the formula

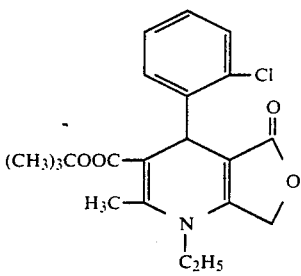

7. A compound according to claim 1, wherein such compound is t-butyl 4-(2-chlorophenyl)-1-ethyl-2-methyl-5-oxo-1,4,5,7-tetrahydrofuro[3,4-b]pyridine-3-carboxylate of the formula

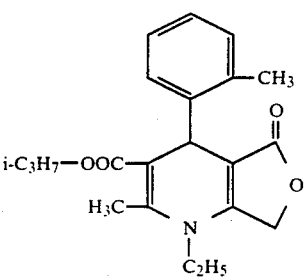

8. A compound according to claim 1, wherein such compound is isopropyl 4-(2-methylphenyl)-1-ethyl-2-methyl-5-oxo-1,4,5,7-tetrahydrofuro[3,4-b]pyridine-3-carboxylate of the formula 9. A compound according to claim 1, wherein such compound is isopropyl 4-(2-cyanophenyl)-1-ethyl-2-methyl-5-oxo-1,4,5,7-tetrahydrofuro[3,4-b]pyridine-3-carboxylate of the formula

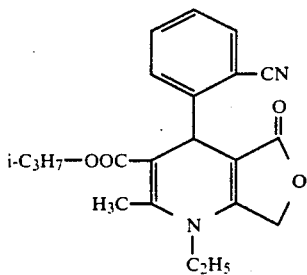

10. A blood sugar lowering composition comprising a blood sugar lowering effective amount of a compound according to claim 1 in admixture with a diluent.

11. A unit dose of a composition according to claim 10 in the form of a tablet, capsule or ampule.

12. A method of lowering a patient's blood sugar level which comprises administering to such patient a blood sugar lowering effective amount of a compound according to claim 1.

13. The method according to claim 12, wherein such compound is:

ethyl 4-(2-chlorophenyl)-1-ethyl-2-methyl-5-oxo-1,4,5,7-tetrahydrofuro[3,4-b]pyridine-3-carboxylate, isopropyl 4-(2-chlorophenyl)-1-ethyl-2-methyl-5-oxo-1,4,5,7-tetrahydrofuro[3,4-b]pyridine-3-carboxylate, ethoxyethyl 4-(2-chlorophenyl)-1-ethyl-2-methyl-5-oxo-1,4,5,7-tetrahydrofuro[3,4-b]pyridine-3-carboxylate, t-butyl 4-(2-chlorophenyl)-1-ethyl-2-methyl-5-oxo-1,4,5,7-tetrahydrofuro[3,4-b]pyridine-3-carboxylate, isopropyl 4-(2-methylphenyl)-1-ethyl-2-methyl-5-oxo-1,4,5,7-tetrahydrofuro[3,4-b]pyridine-3-carboxylate or isopropyl 4-(2-cyanophenyl)-1-ethyl-2-methyl-5-oxo-1,4,5,7-tetrahydrofuro[3,4-b]pyridine-3-carboxylate.

* * * * *

UNITED STATES PATENT AND TRADEMARK OFFICE
CERTIFICATE OF CORRECTION

PATENT NO. : 5,026,714

DATED : June 25, 1991

INVENTOR(S) : Goldmann et al.

It is certified that error appears in the above-identified patent and that said Letters Patent is hereby corrected as shown below:

Title page:

Item (56)  U.S. PATENT DOCUMENTS:  Delete " 4,253,248 " and substitute -- 4,532,248 --

Signed and Sealed this

Fourth Day of May, 1993

Attest:

MICHAEL K. KIRK

Attesting Officer   Acting Commissioner of Patents and Trademarks